(12) United States Patent
Sakowicz (10) Patent No.: US 6,613,540 B1
(45) Date of Patent: *Sep. 2, 2003

(54) METHODS FOR SCREENING AND THERAPEUTIC APPLICATIONS OF KINESIN MODULATORS

(75) Inventor: Roman Sakowicz, Foster City, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/174,594

(22) Filed: Jun. 18, 2002

Related U.S. Application Data (63) Continuation of application No. 09/594,668, filed on Jun. 15, 2000, now Pat. No. 6,440,686.

(51) Int. Cl.[7] ................................................. C12Q 1/42

(52) U.S. Cl. ............................... 435/21; 435/18; 435/29

(58) Field of Search ............................... 435/4, 18, 21, 435/29

(56) References Cited

U.S. PATENT DOCUMENTS

| | | | |
|---|---|---|---|
| 6,207,403 B1 | 3/2001 | Goldstein et al. | 435/21 |
| 6,440,686 B1 * | 8/2002 | Sakowicz | 435/21 |

FOREIGN PATENT DOCUMENTS

| | | | |
|---|---|---|---|
| WO | WO 95/18857 | 7/1995 | C12N/15/12 |
| WO | WO 99/34806 | 7/1999 | A61K/31/56 |
| WO | WO 00/63353 | 10/2000 | C12N/9/16 |
| WO | WO 00/07017 | 2/2001 | G01N/33/50 |
| WO | WO 01/07602 | 2/2001 | C12N/15/11 |

OTHER PUBLICATIONS

Mayer et al. (1999) Science 286:971–4 "Small molecule inhibition of mitotic spindle bipolarity identified in phenotype–based screens".
Blangy et al. (1997) J Biol Chem 272:19418–24 "Phosphorylation by p34cdc2 protein kinase regulates binding of the kinesin–related motor HsEg5 to the dynactin subunit p 150".
Blangy et al. (1998) Cell Motil Cytoskeleton 40:174–82 "Rigor–type mutation in the kinesin–related protein HsEg5 changes its subcellular localization and induces microtubule bundling".
Giet et al. (1999) J Biol Chem 274:15005–13 "The Xenopus Iaevis aurora–related protein kinase pEg2 associates with and phosphorylates the kinesin–related protein X1Eg5".
Kapoor et al. (1999) Proc Natl Acad Sci U S A 96:9106–11 "Allele–specific activators and inhibitors for kinesin".
Lockhart et al. (1996) Biochemistry 35:2365–73 "Kinetics and motility of the Eg5 microtubule motor".
Hackney (1994) J. Biol. Chem. 269:16508–16511 "The rate–limiting step in microtubule–stimulated ATP hydrolysis by dimeric kinesin head domains occurs while bound to the microtubule".
Goldstein (1993) Annu. Rev. Genet. 27:319–351 "With apologies to Scheherazade: Tails of 1001 kinesin motors".
Desai et al. (1999) Cell 96:69–78 "Kin I kinesins are microtubule destabilizing enzymes".
Walczak et al.(1996) Cell 84:37–4.7 "XKCM1: A Xenopus kinesin–related protein that regulates microtubule dynamics during mitotic spindle assembly".
Whitehead et al. (1995) GenBank Accession Number U37426, versions 1151084 and 1171152.
Whitehead et al. (1996) Arthritis and Rheumatism 39:1635–1642 "The spindle kinesin–like protein HsEgS is an autoantigen in systemic lupus erythematosus".
Le Guellec et al. (1991) Mol. Cell BioL 11:3395–3398 "Cloning by differential screening of a Xenopus cDNA that encodes a kinesin–related protein".
Cole et al. (1994) J. Biol. Chem. 269:22913–22916 "A "Slow" homotetrameric kinesin–related motor protein purified from Drosophila embryos".
Blangy et al. (1995) Cell 83:1159–69, "Phosphorylation by p34cdc2 regulates spindle association of human Eg5, a kinesin–related motor essential for bipolar spindle formation in vivo".
Drummond et al. (1998) J. Cell Sci. 111:853–65 "Mutations in the bimC box of Cut7 indicate divergence of regulation within the bimC family of kinesin related proteins".
Gaglio et al. (1996) J. Cell Biol. 135:399–414 "Opposing motor activities are required for the organization of the mammalian mitotic spindle pole".
Heck et al. (1993) J. Cell Biol. 123:665–79 "The kinesin––like protein KLP61F is essential for mitosis I Drosophila".
Hoyt et al. (1992) J. Cell Biol. 118:109–120 "Two S. cerevisiae kinesin–related gene products required for mitotic spindle assembly".
Kashina et al. (1996) Nature 379:270–2 "A bipolar kinesin".
Kashina et al. (1997) Biochim. Biophys. Acta 1357:257–71 "The bimC family of kinesins: essential bipolar mitotic motors driving centrosome separation".
Roof et al. (1992) J. Cell Biol. 188:95–108 "Kinesin–related proteins required for assembly of the mitotic spindle".
Sawin et al. (1992) Nature 359:540–3 "Mitotic spindle organization by a plus–end–directed microtubule motor".

(List continued on next page.)

Primary Examiner—Ralph Gitomer
(74) Attorney, Agent, or Firm—Lauren L. Stevens; Townsend & Townsend & Crew LLP (57) ABSTRACT

The present invention relates to protein modulators, especially modulators of kinesin bioactivities. The present invention provides methods for screening protein modulators, e.g., kinesin modulators that bind to a region of a kinesin and/or that modulate kinesin bioactivities. The present invention also provide methods and compositions for treatment of disorders mediated by abnormal cellular proliferation activities.

16 Claims, 3 Drawing Sheets

OTHER PUBLICATIONS

Sawin et al. (1995) Proc. Natl. Acad. Sci. USA 92:4289–93 "Mutations in the kinesin–like protein disrupting localization to the mitotic spindle".

Sharp et al. (1999) J. Cell Biol. 144:125–138 "The bipolar kinesin, KLP61F, cross–links microtubules within interpolar microtubule bundles of Drosophila embryonic mitotic spindles".

Walczak et al. (1998) Curr. Biol. 8:903–13 "A model for the proposed roles of different microtubule–based motor proteins in establishing spindle polarity".

Whitehead et al. (1998) J. Cell Sci. 111:2551–61 "Expanding the role of HsEg5 within the mitotic and post–mitotic phases of the cell cycle".

Kaiser et al, "All–transRetonic Acid–mediated Growth Inhibition Involves Inhibition of Human Kinesin–related Protein HsEg5", Jul. 1999, The Journal of Biological Chemistry, vol. 274, No. 27, Issue of Jul. 2, 1999, pp 18925–18931.

Hopkins, Seth C. et al. "Inhibitors of Kinesin Activity from Structure–Based Computer Screening", Feb. 18, 2000, Bichemistry 2000, 39, pp 2805–2814.

* cited by examiner-

METHODS FOR SCREENING AND THERAPEUTIC APPLICATIONS OF KINESIN MODULATORS

This is a Continuation application of prior application Ser. No. 09/594,668 filed on Jun. 15, 2000, now U.S. Pat. No. 6,440,686 the disclosure of which is incorporated herein by reference.

FIELD OF THE INVENTION

The invention resides in the fields of molecular biology and medicine, and more particularly drug discovery.

BACKGROUND OF THE INVENTION

The kinesin superfamily are comprised of proteins which utilize a conserved catalytic motor domain to generate intracellular movement of vesicles or macromolecules along microtubules in diverse eukaryotic cellular processes (e.g., cell proliferation). Over 90 kinesin proteins can be classified into at least 8 subfamilies based on primary amino acid sequence, domain structure, velocity of movement, and cellular function. The motor domain is a compact structure of approximately 340 amino acids, and can be located at the N-terminus, in the internal region, or at the C-terminus of the kinesin molecule. Most of the kinesin proteins have an N-terminal catalytic motor domains, e.g., the BimC and the KHC families (See, e.g., Goldstein et al., Annu. Rev. Cell Dev. Biol., 15:141–83,1999; Moore, J. D. and Endow, S. A., Bioassays 18:207–219, 1996). During mitosis, kinesins organize microtubules into the bipolar structure that is the mitotic spindle, mediate movement of chromosomes along spindle microtubules, as well as structural changes in the mitotic spindle associated with specific phases of mitosis. These "molecular motors" translate energy released by hydrolysis of ATP into mechanical force which drives the directional movement of cellular cargoes along microtubules.

The prototypical native kinesin molecule is a heterotetramer comprised of two heavy polypeptide chains (KHC's) and two light polypeptide chains (KLC's). The KHC homodimer is typically referred to as "kinesin" and is classified as a member of the KHC kinesin family (Goldstein et al., Annu. Rev. Cell Dev. Biol., 15:141–83,1999). The human form of KHC has been cloned (Navone et al., J. Cell Biol., 117:1263–75 (1992)). Human KHC N-terminal fragments have reportedly been expressed in *E. coli.*, and purified (Fujiwara, et al., Biophys. J. 69:1563–8, 1995; Vale et al., Nature 380:451–3, 1996). Crystal structure of KHC motor domain has been reported (Kull et al., Nature 380:550–555, 1996). Motility activity of KHC has also been reported.

Another notable kinesin that has been identified is kinesin-like spindle protein ("KSP"), a member of the BimC kinesin family that is characterized by a conserved, globular motor domain at the amino terminus followed by a non-conserved, rod-like helical coiled-coil domain and a BimC box at the carboxyl terminus (Endow, Trends Biol. Sci. 16:221–225, 1991; Sanders et al., J. Cell Biol. 128:617–624, 1995). During mitosis, KSP associates with microtubules of the mitotic spindle. Microinjection of antibody directed against KSP into human cells prevents spindle pole separation during prometaphase, giving rise to monopolar spindles and causing mitotic arrest. KSP and related kinesins bundle antiparallel microtubules and slide them relative to one another, thus forcing the two spindle poles apart. KSP may also mediate in anaphase B spindle elongation and focusing of microtubules at the spindle pole.

Human KSP (also termed HsEg5) has been cloned and characterized (see, e.g., Blangy et al., Cell, 83:1159–69 (1995); Galgio et al., J. Cell Biol., 135:399–414, 1996; Whitehead et al., J. Cell Sci., 111:2551–2561, 1998; Kaiser, et al., J. Biol. Chem., 274:18925–31, 1999; GenBank accession numbers: X85137, NM 004523). Drosophila (Heck et al., J. Cell Biol., 123:665–79, 1993) and Xenopus (Le Guellec et al., Mol. Cell Biol., 11:3395–8, 1991) homologs of KSP have been reported. Drosophila KLP61F/KRP130 has reportedly been purified in native form (Cole, et al., J. Biol. Chem., 269:22913–22916, 1994), expressed in *E. coli,*(Barton, et al., Mol. Biol. Cell, 6:1563–74, 1995) and reported to have motility and ATPase activities (Cole, et al., supra; Barton, et al., supra). Xenopus Eg5 was expressed in *E. coli* and reported to possess motility activity (Sawin, et al., Nature, 359:540–3, 1992; Lockhart and Cross, Biochemistry, 35:2365–73, 1996; Crevel, et al, J. Mol. Biol., 273:160–170, 1997) and ATPase activity (Lockhart and Cross, supra; Crevel et al., supra).

Besides KSP, other members of the BimC family include BimC, CIN8, cut7, KIP1, KLP61 F (Barton et al., Mol. Biol. Cell. 6:1563–1574, 1995; Cottingham & Hoyt, J. Cell Biol. 138:1041–1053, 1997; DeZwaan et al., J. Cell Biol. 138:1023–1040, 1997; Gaglio et al., J. Cell Biol. 135:399–414, 1996; Geiser et al., Mol. Biol. Cell 8:1035–1050, 1997; Heck et al., J. Cell Biol. 123:665–679, 1993; Hoyt et al., J. Cell Biol. 118:109–120, 1992; Hoyt et al., Genetics 135:35–44, 1993; Huyett et al., J. Cell Sci. 111:295–301, 1998; Miller et al., Mol. Biol. Cell 9:2051–2068, 1998; Roof et al., J. Cell Biol. 118:95–108, 1992; Sanders et al., J. Cell Biol. 137:417–431,1997; Sanders et al., Mol. Biol. Cell 8:1025–0133, 1997; Sanders et al., J. Cell Biol. 128:617–624, 1995; Sanders & Hoyt, Cell 70:451–458, 1992; Sharp et al., J. Cell Biol. 144:125–138, 1999; Straight et al., J. Cell Biol. 143:687–694, 1998; Whitehead & Rattner, J. Cell Sci. 111:2551–2561, 1998; Wilson et al., J. Cell Sci. 110:451–464, 1997).

SUMMARY OF THE INVENTION

The present invention provides a method for identifying an agent as a modulator of a kinesin. This method exploits the finding that loop 5 of the KSP motor domain is a binding site for a variety of test agents. The method comprises contacting a L5 loop-containing polypeptide with a test agent; and detecting a signal indicating binding between the test agent and the L5 loop.

According to a particularly preferred embodiment, the L5 loop-containing polypeptide is KSP or a fragment thereof, such as the motor domain of KSP. According to one aspect of the invention, the signal that is detected is fluorescence from a tryptophan residue within the L5 loop with a reduction of fluorescence following contacting the L5 loop with the test agent indicating binding of the test agent to the L5 loop.

Another aspect of the invention provides for a competitive binding assay, wherein the L5 loop containing polypeptide is contacted with a compound known to bind the L5 loop in addition to the test agent, and the signal indicates that the test agent competes with the compound for binding to the L5 loop.

According to another aspect of the invention, the method further comprises contacting the identified kinesin modulator with a kinesin molecule or a cell comprising a kinesin molecule, and determining an effect of the modulator on a bioactivity of said kinesin. In a particularly preferred embodiment, the bioactivity is mitosis, ATP hydrolysis or bipolar spindle formation and the effect can be evidenced on cellular proliferation, cellular viability, motility, or morphology. In a more preferred embodiment, the modulator inhibits the bioactivity of KSP and produces a monopolar spindle phenotype.

The invention also provides a method of inhibiting cellular proliferation, comprising administering to a cell a composition comprising a kinesin modulator identified with the above method, thereby inhibiting proliferation of the cell.

A further aspect of the invention is drawn to a method for treating a disease in a patient, comprising administering to said patient a composition comprising an effective amount of kinesin modulator that specifically binds to the L5 loop region of a kinesin, and more preferably, of KSP, thereby treating said patient.

The invention also provides a fragment of a kinesin polypeptide comprising a L5 loop region of KSP.

DETAILED DESCRIPTION

I. Introduction

The present invention provide methods for screening test compounds for capacity to modulate the bioactivities of kinesin molecules and more preferably, of KSP. These methods are premised, in part, on the discovery by the present inventors that a number of structurally different compounds bind to loop-5 of KSP and thereby modulate the bioactivity of KSP. Accordingly, other compounds can be tested for modulation activity by a simple binding assay that determines whether a compound specifically binds to the loop-5 region. For compounds binding to the loop-5 region, presence of modulation activity can then be confirmed with a bioactivity assay. Such an assay also reveals the nature of modulation (i.e. inhibition or stimulation) and extent of modulation achieved by a compound.

Compounds having modulation activity are useful for controlling cellular proliferation. Kinesins play important roles in cell proliferation, e.g., ATP hydrolysis and microtubule sliding, spindle formation and spindle pole separation. Numerous diseases or disorders are at least partially attributed to cellular proliferation activities, e.g., cancers, autoimmune diseases, or proliferation induced after medical procedures. For example, in some methods, pharmaceutic compositions containing the kinesin modulators are administered to patients with the diseases, and the symptoms are eliminated or alleviated by modulating cellular proliferation activities. In other methods, stimulation of cellular proliferation is desired. For example, such is useful for culturing cells producing a pharmaceutical protein in vitro where the goal is to produce large amounts of protein. Such is also useful in therapeutic methods in which a patient receives a transplant of cells, such as bone marrow stem cells, and it is desired that the cells proliferate and/or differentiate in situ after transplantation.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). Although any methods and materials similar or equivalent to those described herein can be used in the practice or testing of the present invention, the preferred methods and materials are described. The following definitions are provided to assist the reader in the practice of the invention.

The term "agent" includes any substance, molecule, element, compound, entity, or a combination thereof. It includes, but is not limited to, e.g., protein, oligopeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "antibody" or "immunoglobulin" is used to include intact antibodies and binding fragments thereof. Typically, fragments compete with the intact antibody from which they were derived for specific binding to an antigen fragments including separate heavy chains, light chains Fab, Fab', F(ab')2, Fabc, and Fv. Fragments are produced by recombinant DNA techniques, or by enzymatic or chemical separation of intact immunoglobulins. The term "antibody" also includes one or more immunoglobulin chain that are chemically conjugated to, or expressed as, fusion proteins with other proteins. The term "antibody" also includes bispecific antibody. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315–321 (1990); Kostelny et al., *J. Immunol.* 148, 1547–1553 (1992).

The term "antisense molecules" include antisense or sense oligonucleotides comprising a single-stranded nucleic acid sequence (either RNA or DNA) capable of binding to target mRNA (sense) or DNA (antisense) sequences for a specific protein (e.g., a kinesin). The ability to derive an antisense or a sense oligonucleotide, based upon a cDNA sequence encoding a given protein is described in, e.g., Stein and Cohen (Cancer Res. 48:2659, 1988) and van der Krol et al. (BioTechniques 6:958, 1988).

A "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, chemical means and the like.

The term "epitope" or "antigenic determinant" refers to a site on an antigen to which B and/or T cells respond. Bell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallogaraphy and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13–15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110–19 (1994)), by antigen-dependent killing (cytotoxic T lymphocyte assay, Tigges et al., *J. Immunol.* 156, 3901–3910) or by cytokine secretion.

The term "fusion protein" refers to a composite polypeptide, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art.

The term "functional derivative" of a native protein or a polypeptide is used to define biologically active amino acid sequence variants that possess the bioactivities that are substantially similar to those of the reference protein or polypeptide. Depending on the circumstances, a functional derivative of kinesin can retain one or more of its bioactivities.

The term "modulation" refers to both upregulation, (i.e., activation or stimulation) and downregulation (i.e. inhibition or suppression) of a bioactivity (e.g., cellular proliferation activity, motility, ATPase activity).

A "patient" includes both humans and other animals (particularly mammals) and other organisms that receive either prophylactic or therapeutic treatment.

By "randomized" is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized proteinaceous test agents. The library can be fully randomized, with no sequence preferences or constants at any position.

The term "substantial identity" means that two peptide sequences, when optimally aligned, such as by the programs GAP or BESTFIT using default gap weights, share at least 65 percent sequence identity, preferably at least 80 or 90 percent sequence identity, more preferably at least 95 percent sequence identity or more (e.g., 99 percent sequence identity or higher). Preferably, residue positions which are not identical differ by conservative amino acid substitutions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis. ), or by visual inspection (see generally Ausubel et al., supra). One example of algorithm that is suitable for determining percent sequence identity and sequence similarity is the BLAST algorithm, which is described in Altschul et al., *J. Mol. Biol.* 215:403–410 (1990). Software for performing BLAST analyses is publicly available through the National Center for Biotechnology Information (http://www.ncbi.nlm.nih.gov/). Typically, default program parameters can be used to perform the sequence comparison, although customized parameters can also be used. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89, 10915 (1989))

For purposes of classifying amino acids substitutions as conservative or nonconservative, amino acids are grouped as follows: Group I (hydrophobic side chains): Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

Therapeutic agents of the invention are typically substantially pure from undesired contaminant. This means that an agent is typically at least about 50% w/w (weight/weight) purity, as well as being substantially free from interfering proteins and contaminants. Sometimes the agents are at least about 80% w/w and, more preferably at least 90 or about 95% w/w purity. However, using conventional protein purification techniques, homogeneous peptides of at least 99% w/w can be obtained.

"Specific binding" between two entities means an affinity of at least $10^6$, $10^7$, $10^8$, $10^9$ M$^{-1}$, or $10^{10}$ M$^{-1}$. Affinities greater than $10^8$ M$^{-1}$ are preferred.

The term "test agent" as used herein describes any molecule, e.g., protein, oligopeptide, small organic molecule, polysaccharide, polynucleotide, etc., that can be screened for their capability of directly or indirectly altering the bioactivities of kinesin.

A "variant" of a kinesin refers to kinesin polypeptide amino acid sequence that is altered by one or more amino acid residues relative to the wild type kinesin sequence. Unless otherwise specified, the term "analog" can be used interchangeably with "variant". A variant can be an allelic variant, a species variant, or an induced variant. The variant can have "conservative" changes, wherein a substituted amino acid has similar structural or chemical properties (e.g., replacement of leucine with isoleucine). Alternatively, a variant can have "nonconservative" changes (e.g., replacement of glycine with tryptophan). Analogous minor variations can also include amino acid deletions or insertions, or both. Guidance in determining which amino acid residues can be substituted, inserted, or deleted without abolishing biological or immunological activity can be found using computer programs well known in the art, for example, LASERGENE™ software.

III. Methods for Identifying Kinesin Modulators by Detecting Binding to L5 Region A. Kinesins and L5 Region of Kinesins The kinesin motor domain has a single α/β arrow-head-shaped structure. It has a core eight-stranded, mostly parallel β-sheet that is flanked on each side by three α-helices. Various loop structures separate the β-sheets or α-helices (see, e.g., Kull et al., Nature 380:550–555, 1996; Sack et al., Biochemistry 36:16155–16165, 1997; and Gulick et al., Biochemistry 37:1769–1776, 1998). These secondary loop structures are each formed by a segment of contiguous amino acids in the primary structure of a kinesin molecule. "L5", "L5 loop", or "Loop 5" is a conventional term for the fifth of such segments numbered from the N-terminal of the motor domain.

The L5 loop, which is found in all members of the kinesin superfamily, plays an important role in kinesin ATPase activity. The L5 regions of many kinesins are already known. For example, in the kinesin KSP, the loop 5 region occurs from Gly$^{117}$ to Gly$^{134}$ inclusive (with the N-terminal amino acid of mature KSP being designated amino acid 1). (See, direct Genback submission, Whitehead et al., submitted 29-SEP-1995 by Clark Medical Biochemistry Department, University of Calgary, 3330 Hospital dr. NW, Calgary, Alberta T2N 4N1, Cannda, Locus HSU37426, Accession #U37426 or locus HSKINRELP; Accession #X85137 for the sequence of KSP.) The L5 region of KHC occurs from Glu$^{96}$-Gly$^{106}$, that of ncd from Asp$^{445}$-Gly$^{452}$, and that of Kar3 from Leu$^{485}$-Gly490 (Gulick et al., Biochemistry 37:1769–1776, 1998). For other kinesins, such regions can be determined by, e.g., sequence alignment or structural analysis using methods well known in the art (e.g., X-ray crystallography or computer modeling).

The present screening methods employ the loop 5 region of natural human kinesins, and allelic, species and induces variants thereof. Typically, the loop-5 region of such variants differs from that of a natural human loop 5 region by one or a few conservative modifications. Typically, the loop region of such variants show at least 85% sequence identity at the amino acid level to a natural human loop-region. Species variants include kinesins of Xenopus, Drosophila and other insects, plants, fungi, and various other mammalian species. Some kinesins used in the screening methods include unnatural amino acids (e.g., D-lysine in place of L-lysine to generate more stable peptides). Similarly, modification of the amino or carboxyl terminals can also be used to confer stabilizing properties upon the polypeptides of the invention, e.g. amidation of the carboxyl-terminus or acylation of the amino-terminus or pegylated derivatives.

Some screening methods of invention employ an intact loop 5. In some methods, a loop-5 region is used without other kinesin sequences. In some methods, the loop 5 region is contained within flanking sequences of a kinesin molecule. In some methods, the loop-5 region is contained within a fragment of a kinesin molecule. In some methods, the loop 5 region is contained within a full length kinesin molecule. In some methods, the loop 5 region is contained within a motor domain of a kinesin molecule. In some methods, an active fragment of a loop 5 region retaining at least one bioactivity of an intact loop 5 region is used. Usually, loop-5 polypeptides used in the screening methods contain at least 4, 6, 8, 10, 12, or 14 contiguous amino acid residues of the L5 region of a kinesin. Typically, a L5-containing polypeptide comprises between about 5 to about 200 amino acid residues. Preferably, a L5-containing polypeptide comprises between 5 to 100 amino acids residues; more preferably, between about 5 to about 50 amino acid residues; and most preferably, between about 5 to about 20 amino acid residues.

In a particularly preferred embodiment, the L5-containing polypeptide comprises the L5 region of KSP.

Kinesins or their fragments (e.g., a L5-containing polypeptide) can be obtained by recombinant expression in a host cell of nucleic acids encoding the polypeptides, by in vitro expression, by chemical peptide synthesis or can be obtained from natural sources, among other methods. Methods of production and purification of kinesins and fragments thereof are also described in commonly-owned U.S. Ser. No. 09/295,612, entitled "Human Kinesins and Methods of Producing and Purifying Human Kinesins."

B. Test Agents and Anti-L5 Antibodies

Test agents that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Usually, test compounds are organic. Some test compounds are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

Libraries of test agents to be screened with the claimed methods can also be generated based on structural studies of a target kinesin molecule. Such structural studies allow the identification of test agents that are more likely to bind to the L5 loop of the target kinesin. The three-dimensional structure of kinesins can be studied in a number of ways, e.g., crystal structure and molecular modeling. Methods of studying protein structures using x-ray crystallography are well known in the literature. See Physical Biochemistry, Van Holde, K. E. (Prentice-Hall, New Jersey 1971), pp.221–239, and Physical Chemistry with Applications to the Life Sciences, D. Eisenberg & D. C. Crothers (Benjamin Cummings, Menlo Park 1979). Computer modeling of kinesin structures provides another means for designing test compounds for screening kinesin modulators. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NER of Proteins and Nucleic Acids, K. Wuthrich (Wiley-lnterscience, New York 1986).

Kinesin modulators of the invention also include antibodies that specifically bind to L5 (anti-L5 antibodies). Such antibodies can be monoclonal or polyclonal. Such antibodies can be generated using loop 5 region or a kinesin containing the same as the immunogen. Methods for producing antibodies are well known in the art. For example, the production of non-human monoclonal antibodies, e.g., murine or rat, can be accomplished by, for example, immunizing the animal with a L5 fragment (See Harlow & Lane, Antibodies, A Laboratory Manual, Cold Spring Harbor Laboratory Press, Cold Spring Harbor N.Y.). Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029–10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to L5 fragment.

Human antibodies against L5 can also be produced from non-human transgenic mammals having transgenes encoding at least a segment of the human immunoglobulin locus and an inactivated endogenous immunoglobulin locus. See, e.g., Lonberg et al., WO 93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using L5 fragment or other amyloid peptide as an affinity reagent.

C. Assays for Detecting Binding Between a Test Agent and L5-Containing Polypeptide Binding of a test agent to a L5-containing polypeptide is determined in a reaction mixture. Typically, microtubules are also present in the reaction mixture. A control is usually performed in which microtubules are omitted. Usually, the loop 5 region is obtained from the kinesin molecule for which modulation is ultimately desired.

Binding can be assayed by a number of methods including e.g., labeled in vitro protein-protein binding assays, electrophoretic mobility shift assays, immunoassays for protein binding, functional assays (phosphorylation assays, etc.) and the like. See, e.g., U.S. Pat. Nos. 4,366,241; 4,376,110; 4,517,288; and 4,837,168, and also Bevan et al., Trends in Biotechnology 13:115–122, 1995; Ecker et al., Bio/Technology 13:351–360, 1995; and Hodgson, Bio/Technology 10:973–980, 1992. The test agent can be identified by detecting a direct binding to the L5-containing polypeptide, e.g., co-immunoprecipitation of with the L5-containing polypeptide by an anti-L5 antibody. The test agent can also be identifiecd by detecting a signal that indicates that the agent binds to the L5-containing polypeptide, e.g., fluorescence quenching. In some methods, in which binding is determined to an L5 fragment free or substantially free of kinesin flanking sequences, it is not necessary to localize where on the kinesin molecule the test compound binds. In other methods, in which L5 is provided as a longer protein, optionally including other kinesin flanking sequences, an assay is employed which distinguishes between binding to the L5 region and the flanking regions of the protein.

Competition assays provide a suitable format for identifying test compounds that specifically bind to the L5 region. In such formats, test compounds are screened in competition with a compound already known to bind to the L5 region. The known L5-binding agent can be a synthetic kinesin inhibitor, e.g., the representative KSP inhibitors shown in FIG. 1 (see Examples, infra). It can also be an antibody which specifically recognizes the L5 epitope, e.g., a monoclonal antibody directed against the L5 fragment. If the test compound inhibits binding of the compound known to bind L5, then the test compound also binds L5.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242–253 (1983)); solid phase direct biotin-avidin EIA (see Kirkland et al., J. Immunol. 137:3614–3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using I-125 label (see Morel et al., Mol. Immunol. 25(1):7–15 (1988)); solid phase direct biotin-avidin EIA (Cheung et al., Virology 176:546–552 (1990)); and direct labeled RIA (Moldenhauer et al., Scand. J. Immunol. 32:77–82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

The screening assays can be either in insoluble or soluble formats. One example of the insoluble assays is to immobilize kinesin molecules or their fragments onto a solid phase matrix. The solid phase matrix is then put in contact with test agents, in the presence or absence of microtubules, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing the kinesin molecule, the test agents are bound to the solid matrix and the kinesin molecule is then added.

Soluble assays include some of the combinatorial libraries screening methods and the genetic screening systems described above. Under the soluble assay formats, neither the test agents nor the kinesin molecules are bound to a solid support. Binding of a kinesin molecule or fragment thereof to a test agent can be determined by, e.g., changes in fluorescence of either the kinesin molecule or the test agents, or both. Fluorescence may be intrinsic or conferred by labeling either component with a fluorophor. Binding can be detected by fluorescence polarization. For example, KSP inhibitors can be screened by monitoring fluorescence of $Trp^{127}$ in the L5 region, as described in Example. Such fluorescence measurement provide a measure of specific binding to the loop 5 region.

In some binding assays, either the L5-containing polypeptide, the test agent, or a third molecule (e.g., an anti-L5 antibody) as labeled entities, ie., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}I$, $^{32}P$, $^{35}S$) or a chemiluminescent or fluorescent group. Similarly, the detectable group can be a substrate, cofactor, inhibitor or affinity ligand.

Some test compounds with specific binding activity to loop 5 identified by such assays are specific to the loop 5 region of a particular kinesin and can be used to modify the activity of only that kinesin. Other test compounds show specific binding to a plurality of kinesins and can be used to modulate the activity of all of these kinesins.

IV. Methods for Screening Kinesin Modulators by Monitoring Kinesin Bioactivities Binding of a test compound to the loop 5 region provides an indication that the compound is a modulator of kinesin activity. The existence, nature and extend of such activity can then be tested by an activity assay. Such assays can also be used independently to identify kinesin modulators which modulate the bioactivities of kinesin proteins. However, the procedure is more efficient if the number of candidate compounds is first reduced by determining specific binding to the loop 5 region. In general, such methods involve adding a test agent to a sample containing a kinesin in the presence or absence of microtubules, and determining an alteration in the bioactivities of the kinesin. The methods include both in vitro screening methods and in vivo screening of cells for alterations in the presence, distribution, activity or amount of kinesin proteins.

A. Kinesin Bioactivities and Cellular Proliferation

The term "kinesin bioactivity" refers to the biochemical and physiological roles played by a kinesin protein in generating force and movement in the diverse functional contexts. It includes the ability to affect ATP hydrolysis, microtubule binding, gliding and polymerization/depolymerization (effects on microtubule dynamics), binding to other proteins of the mitotic spindle, binding to proteins involved in cell-cycle control, or serving as a substrate to other enzymes, such as kinases or proteases and specific kinesin cellular activities (e.g., chromosome congregation, axonal transport). Unless otherwise specified, "bioactivities of kinesin" can be used interchangeably with the term "kinesin activity."

Kinesins play important roles in cellular proliferation. The term "cell proliferation" or "cellular proliferation" refers to cell division rate and/or cell cycle. Cellular proliferation activities (i.e., biological activities associated with cellular proliferation) include kinesin activity, regulation of spindle pole separation, mitosis, mitotic spindle assembly, satisfaction of the mitotic cell cycle checkpoint, cell cycle progression, apoptosis, cell proliferation, mitotic and involvement in tumor growth.

The terms "modulator of kinesin activity" and "kinesin modulator" are used interchangeably and refer to a substance which directly or indirectly modulates a bioactivity of a kinesin. They includes both "activators" and "inhibitors" of kinesins (e.g., KSP). A kinesin "activator" is a substance which causes the kinesin to become more active in one or more of its bioactivities, and thereby increase the cellular proliferation level. The mode of action of the activator can be direct, e.g., through binding the kinesin, or indirect, e.g., through binding another molecule which otherwise interacts with the kinesin. Conversely, a kinesin "inhibitor" is a substance which causes the kinesin to become less active in one or more of its bioactivities, and thereby decrease cellular proliferation level. The reduction can be complete or partial, and due to a direct or an indirect effect. Similarly, the term "modulator of cellular proliferation," or "cellular proliferation modulator," refers to an agent that is able to alter a bioactivity (e.g., bioactivities of kinesin) that is involved in cellular proliferation. The modulators include both "activators" and "inhibitors" of cellular proliferation.

A modulator can interact with its target through a variety of mechanisms. Kinesin-mediated movement along microtubules involves a complex enzymatic cycle that requires coordination of nucleotide turnover with microtubule interaction, and communication between the regions of the motor domain responsible for these two functions. Perturbation of any one of these events will impair kinesin function. From the results described herein, it can be inferred that the binding of a modulator to the Loop 5 of KSP slows the release of ADP from the nucleotide binding site. Moreover, it can be inferred that the binding event interferes with the communication between the nucleotide binding site and the microtubule binding site. As a result, the cell arrests in mitosis. More specifically, when a cell is treated with a modulator that binds Loop 5 of KSP, for example, the cell arrests in mitosis with a monopolar spindle phenotype.

B. Assays For Screening Modulators of Kinesin Bioactivities

The kinesin bioactivities to be modulated in the screening assays include expression of kinesin genes, biochemical activities of expressed kinesin proteins (e.g., motility, ATPase activity, binding to microtubules). Alternatively, the test agent can be identified based on modulation of a cellular proliferation phenotype, e.g., inhibition of cell proliferation, cell or tumor growth arrest, or cell death. Various assays are available to screen kinesin modulators of the present invention, such as the assays described below or those disclosed in the commonly-owned U.S.Ser. No. 09/428,156, entitled "Method of Screening for Modulators of Cell Proliferation and Methods of Diagnosing Cell Proliferation States."

Either intact kinesin proteins or kinesin fragments or analogs can be used in the screening assays. Kinesin fragments to be used in these assays usually retain one or more of the kinesin bioactivities (e.g., ATP hydrolysis, binding to microtubule, binding to kinesin inhibitors, or motility-related activity). Fusion proteins containing such fragments of kinesin can also be used for the screening of test agents. In addition, functional derivatives of kinesins which have amino acid deletions and/or insertions and/or substitutions while maintaining one or more of the kinesin bioactivities can be used in practicing the screening methods of the present invention.

A functional derivative can be prepared from a naturally occurring or recombinantly expressed kinesin by proteolytic cleavage followed by conventional purification procedures known to those skilled in the art. Alternatively, the functional derivative can be produced by recombinant DNA technology by expressing only fragments of the kinesins that retain one or more of their bioactivities.

In some methods, modulators of kinesin activity can be screened using motility assays. Methods of performing motility assays are described in the art (see, e.g., Hall, et al., Biophys. J. 71: 3467–3476, 1996; Turner et al., Anal. Biochem. 242 :20–5, 1996; Gittes et al, Biophys. J. 70:418–29, 1996; Shirakawa et al., J. Exp. Biol. 198:1809 . 15, 1996; and Winkelmann et al., Biophys. J. 68: 2444–53, 1995).

In some methods, kinesin ATPase activity is monitored in the screening assays. Methods for determining ATPase activity are described, e.g., in Stock et al., J. Biol. Chem., 274:14617–23, 1999; Saborido et al., Anal Biochem, 268:79–88 1999; Jiang et al., Biophys J, 68:283S-285S, 1995. Alternatively, the kinesin ATPase activity can be monitored using a coupled assay which measures ADP production. Such method is described in the Examples, infra, and also disclosed in detail in U.S. patent application Ser. No. 09/314,464, entitled "Compositions and Assay Utilizing ADP or Phosphate for Detecting Protein Modulators." Both an increase or a decrease of the activity of the kinesin protein can be measured with such methods.

In some methods, cell growth and viability assays are used to screen kinesin modulators. In such assays, cell populations are monitored for growth and/or viability, often over time and comparing samples incubated with various concentrations of the test agent or without the test agent. Methods for performing such assays have been described in the art (See, e.g., Buster et al., J Cell Sci Suppl, 14:109–15, 1991; Howard et al., Methods Cell Biol., 39: 137–47, 1993; and Pierce et al., Methods Enzymol., 298:154–71, 1998). For example, the kinesin modulators can be identified by monitoring cell death activity using methods such as described by, e.g., Abend et al., Int. J. Radiat. Biol., 67:315–26, 1995; Vermes et al., J. Immunol. Methods, 184:39–51, 1995; and Cohen et al., Annu. Rev. Immunol. 10:267–93, 1992.

The cell growth or viability assays can be performed prior to, concurrent with, or subsequent to exposing the cells to various physiological signals. The physiological signals include hormones, antibodies, peptides, antigens, cytokines, growth factors, action potentials, pharmacological agents including chemotherapeutics, radiation, carcinogenics, or other cells (i.e. cell-cell contacts). Alternatively, the assays can be performed in the absence of such physiological signals. Further, effects of the test agents on cell growth or viability can be determined at different stages of the cell cycle process.

V. Therapeutic Applications

A. Modulating Cellular Proliferation

Many clinical conditions or disease states are linked to abnormal cell proliferation. Accordingly, the present invention provides methods for treating such conditions or disease states by modulating cellular proliferation activities (e.g., kinesin bioactivities). Once a determination has been made regarding the abnormal proliferation state of a cell the compositions of the present invention (e.g., modulators of kinesin activity) can be administered as therapeutic agents.

The cellular proliferation modulator can be an anti-kinesin antibody (e.g., anti-L5 antibody), or other modulator. Usually such modulators are obtained by the screening methods described above. The modulation can be due to an alteration of a bioactivity involved in cellular proliferation, e.g., modulating motor activity. When administered to a cell, such cellular proliferation modulator (e.g., a kinesin inhibitor which binds to L5 region) can reduces or eliminates an endogenous cellular proliferation activity (e.g., kinesin ATPase activity). Methods of administering nucleic acids encoding peptide modulators are described by Brower et al., *Nature Biotechnology*, 16:1304–1305, 1998; Donnelly et al., Annu Rev Immunol, 15:617–48, 1997; as well as PCT/US93/03868, WO 91/04753, or WO 90/10448).

B. Examples of Diseases and Disorders to be Treated

The diseases and disorders that can be treated with the compositions and methods of the present invention include tumors such as skin, breast, brain, cervical carcinomas, testicular carcinomas. The tumors that can be treated with compositions of the present invention include both solid tumors or metastatic tumors. Cancers that can be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma)

Disease states other than cancer which can be treated by the methods and compositions include restenosis, autoimmune disease, arthritis, graft rejection, inflammatory bowel disease, proliferation induced after medical procedures such as surgery, angioplasty, and the like. In some methods, cells not in a hyper or hypo proliferation state (abnormal state) are the subject of treatment. For example, during wound healing, the cells may be proliferating "normally", but proliferation enhancement may be desired. Similarly, in the agriculture arena, cells may be in a "normal" state, but proliferation modulation may be desired to enhance a crop by directly enhancing growth of a crop, or by inhibiting the growth of a plant or organism which adversely affects the crop. Thus, therapeutic applications of the present invention include treatment of individuals afflicted or impending affliction with any one of these disorders or states.

C. Pharmaceutical Compositions: Dosages and Modes of Administration

The kinesin modulators of the present invention can be directly administered under sterile conditions to the patient to be treated. Modulators can be administered alone or as the active ingredient of a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the patient. For example, the kinesin modulator is complexed with carrier proteins such as ovalbumin or serum albumin prior to their administration in order to enhance stability or pharmacological properties such as half-life. Furthermore, therapeutic formulations of this invention can be combined with or used in association with other therapeutic agents.

The therapeutic formulations can be delivered by any effective means which could be used for treatment. Depending on the specific kinesin modulators to be administered, the suitable means include oral, rectal, vaginal, nasal, pulmonary administration, or parenteral (including subcutaneous, intramuscular, intravenous and intradermal) infusion into the bloodstream. In some instances, for example, in the treatment of wounds and inflammation, the kinesin proteins and modulators can be directly applied as a solution or spray.

The pharmaceutical compositions can be prepared in various forms, such as granules, tablets, pills, suppositories, capsules, suspensions, salves, lotions and the like. The concentration of therapeutically active compound in the formulation may vary from about 0.1–100% by weight. Therapeutic formulations are prepared by any methods well known in the art of pharmacy. See, e.g., Gilman et al., eds., Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

The therapeutic formulations can conveniently be presented in unit dosage form and administered in a suitable therapeutic dose. A suitable therapeutic dose can be determined by any of the well known methods such as clinical studies on mammalian species to determine maximum tolerable dose and on normal human subjects to determine safe dosage. Except under certain circumstances when higher dosages may be required, the preferred dosage of a kinesin modulator usually lies within the range of from about 0.001 to about 1000 mg, more usually from about 0.01 to about 500 mg per day.

The preferred dosage and mode of administration of a kinesin modulator (e.g., a KSP inhibitor) can vary for different patients, depending upon factors that can be individually reviewed by the treating physician, such as the condition or conditions to be treated, the choice of composition to be administered, including the particular kinesin modulator, the age, weight, and response of the individual patient, the severity of the patient's symptoms, and the chosen route of administration). As a general rule, the quantity of a kinesin modulator administered is the smallest dosage which effectively and reliably prevents or minimizes the conditions of the patients. Therefore, the above dosage ranges are intended to provide general guidance and support for the teachings herein, but are not intended to limit the scope of the invention.

VII. EXAMPLES

The following examples are provided to further illustrate the present invention. They are not included to limit the invention in any way.

Example 1

Assays for Studying Kinesin Inhibition

The following assay can be used to identify compounds which inhibit microtubule-stimulated ATPase activity of KSP.

KSP was expressed in and isolated from a bacterial-based expression system using the methods described in U.S. Ser. No. 09/295,612, filed Apr. 20, 1999, which is incorporated herein by reference. The KSP constructs comprise the KSP motor domain and varying lengths of the carboxyl-terminal portion of the KSP protein. In some cases, the KSP construct also contain affinity tags (e.g., hexahistidine) to aid in purification.

Two specific solutions were used in the assay. Solution A was prepared by adding 1 mM ATP, 2 mM phosphoenolpyruvate in a working buffer (25 mM Pipes pH 6.8, 2 mM $MgCl_2$, 1 mM EGTA, 1 mM DTT, 5 $\mu$M taxol, 25 ppm Antifoam). The pH of Solution A was adjusted to 6.8 with KOH after all ingredients are added. Solution B contains 0.6 mM NADH, 0.2 mg/ml BSA, 1:100 dilution of PK/LDH mixture from Sigma, 200 $\mu$g/ml microtubules, 100 nM KSP (i.e. ~2.5 $\mu$g/ml).

To initiate the experiment, a DMSO solution of the test compound is prepared at a ratio of about 0.1 to about 10 mg/ml of compound in DMSO. An aliqguot of the DMSO solution (typically around 1 μl) is added to each well of the bottom row of a 96-well half area plate (in duplicate). Control wells contain only DMSO alone. 50 μl of solution A is then added to each well. The solutions are mixed by repeated pipetting, followed by a series of dilution by repeated transferring of 50 μl of solution between rows. The reaction is initiated by adding 50 μl of solution B to each well. The plate is then inserted in the reader, e.g., the Spectramax 340 reader which is available from Molecular Devices, Inc. and absorbance at 340 nM was monitored for 5 min. The observed rate for 50 μl Solution A+50 μl Solution B in a half-area plate should be about 100 mOD/min. Optionally, a series of dilution was made and absorbance was similarly measured.

Similar procedures were used to study the inhibitory effect of test agents on the basal (i.e., not microtubule-dependent) ATPase of KSP. In these assays, microtubules were omitted from Solution B, and KSP concentration was increased to at least 2 mM.

Figure 3:
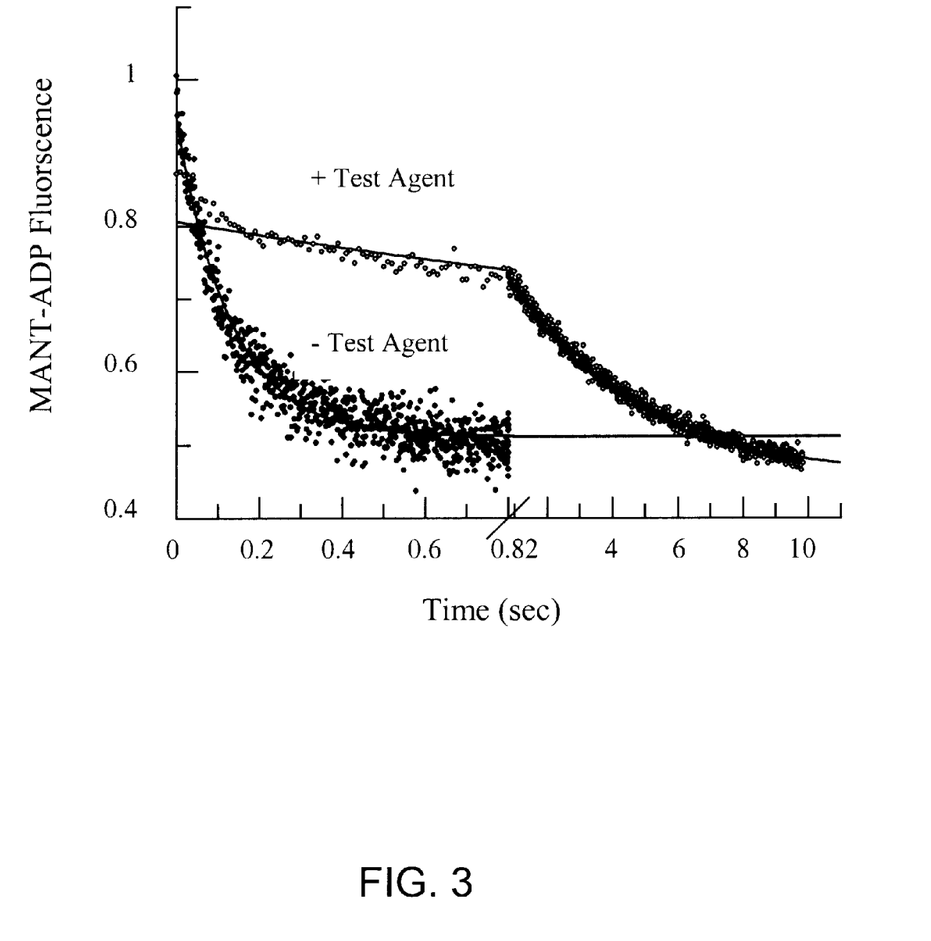
FIG. 3 illustrates the effect of binding of a test agent to KSP on the rate of release of the MANT-ADP nucleotide with the top trace indicating rate of release after treatment with a test agent of FIG. I at a concentration of 7.5 µM with 3 µM KSP and the bottom trace indicating rate of release in the absence of a test agent.

Another assay for studying inhibition of kinesin ATPase activity is the MANT-ADP ("2'(3')-O-(N-methylanthraniloyl) adenosine 5'-diphosphate) labeled release method. KSP was incubated with an excess of MANT-ATP. In the process MANT-ATP replaced ADP bound to the KSP, and was subsequently hydrolyzed to MANT-ADP. Unbound MANT-ATP/ADP was removed by rapid gel filtration. A solution of KSP-MANT-ADP was rapidly mixed in a stopped flow apparatus with 1 mM ATP solution. Release of the MANT-ADP nucleotide off the enzyme was followed by monitoring the decrease in MANT fluorescence. In order to observe microtubule-stimulated MANT-ADP release, microtubules at various concentrations were included in the 1 mM ATP solution. As shown in FIG. 3, binding of a test agent to the KSP construct resulted in a decrease in the rate of release of the MANT-ADP nucleotide.

Additional methods for studying kinesin inhibition are HPLC and fluorescence quenching. HPLC was employed to study direct binding between a test agent and the kinesin. For example, HPLC was used in the present invention to identify test agent which binds to KSP. KSP was preincubated with excess inhibitor and than subjected to a rapid gel filtration on a spin column to separate protein from the unbound inhibitor. The amount of inhibitors remaining with KSP was quantified by separating the spin-column flow through components on a reversed-phase C-8 column, and comparing the peak areas corresponding to the inhibitor and protein. Using this method, it was found that the KSP inhibitors shown in FIG. 1 bind to KSP with a 1:1 stoichiometry, suggesting that members of structurally different classes of KSP inhibitors competed for the same binding site on the KSP molecule.

Figure 2:
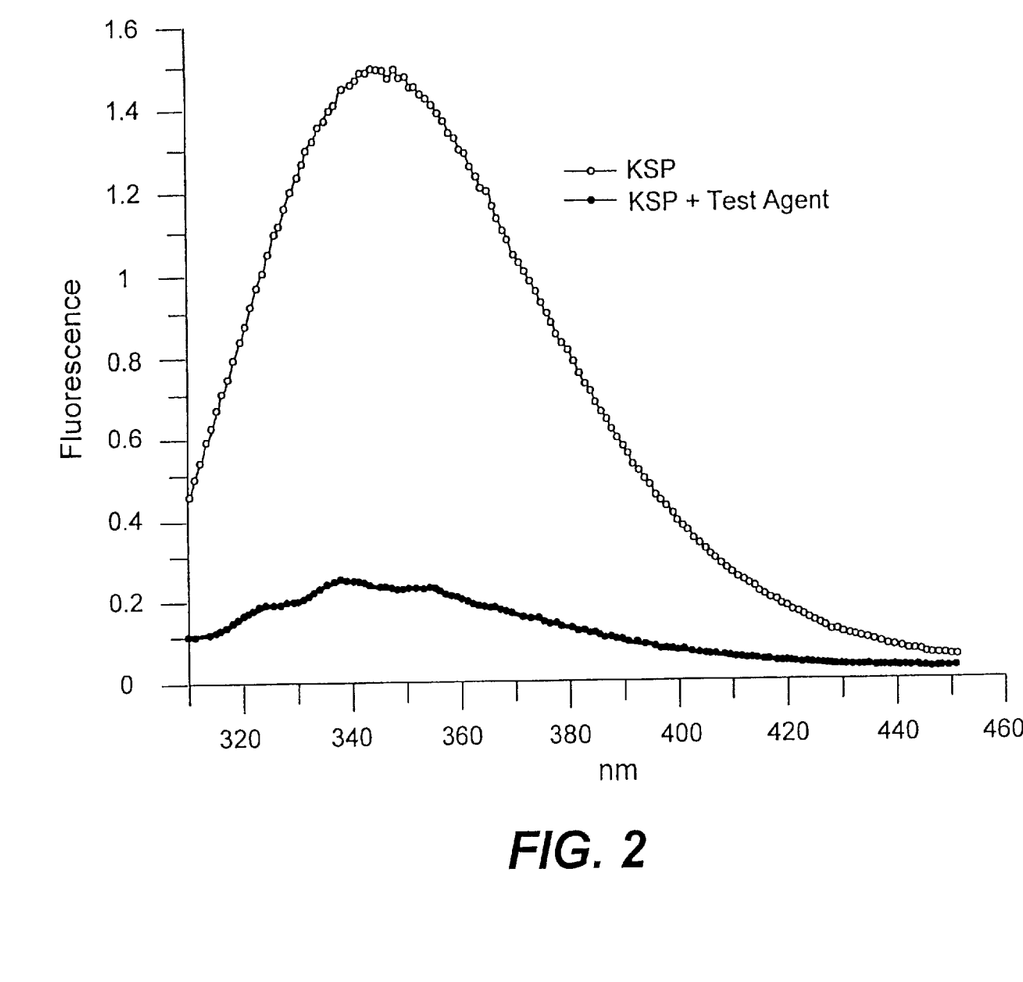
FIG. 2 shows the quenching of the fluorescence of the single tryptophan residue of KSP motor domain as a result of contacting the KSP motor domain with some representative KSP inhibitors.

Similarly, a fluorescence based method was also applied in the present invention to identify kinesin inhibitors. Some of the KSP inhibitors caused a pronounced quenching of the fluorescence of the single tryptophan residue of KSP motor domain (Trp$^{127}$) as shown in FIG. 2. Their binding was followed by a decrease in fluorescence of this tryptophan residue upon mixing protein solution with an inhibitor solution. This experiment can be performed in a stirred cuvette for an equilibrium binding studies, or in a stopped flow apparatus to measure the on-rates of inhibitor binding. These results indicate that the inhibitors' binding site(s) is proximal to the single tryptophan residue of KSP (Trp127), which is located in the L5 loop.

Example 2

Identification and Characterization of KSP Inhibitors

Figure 1:
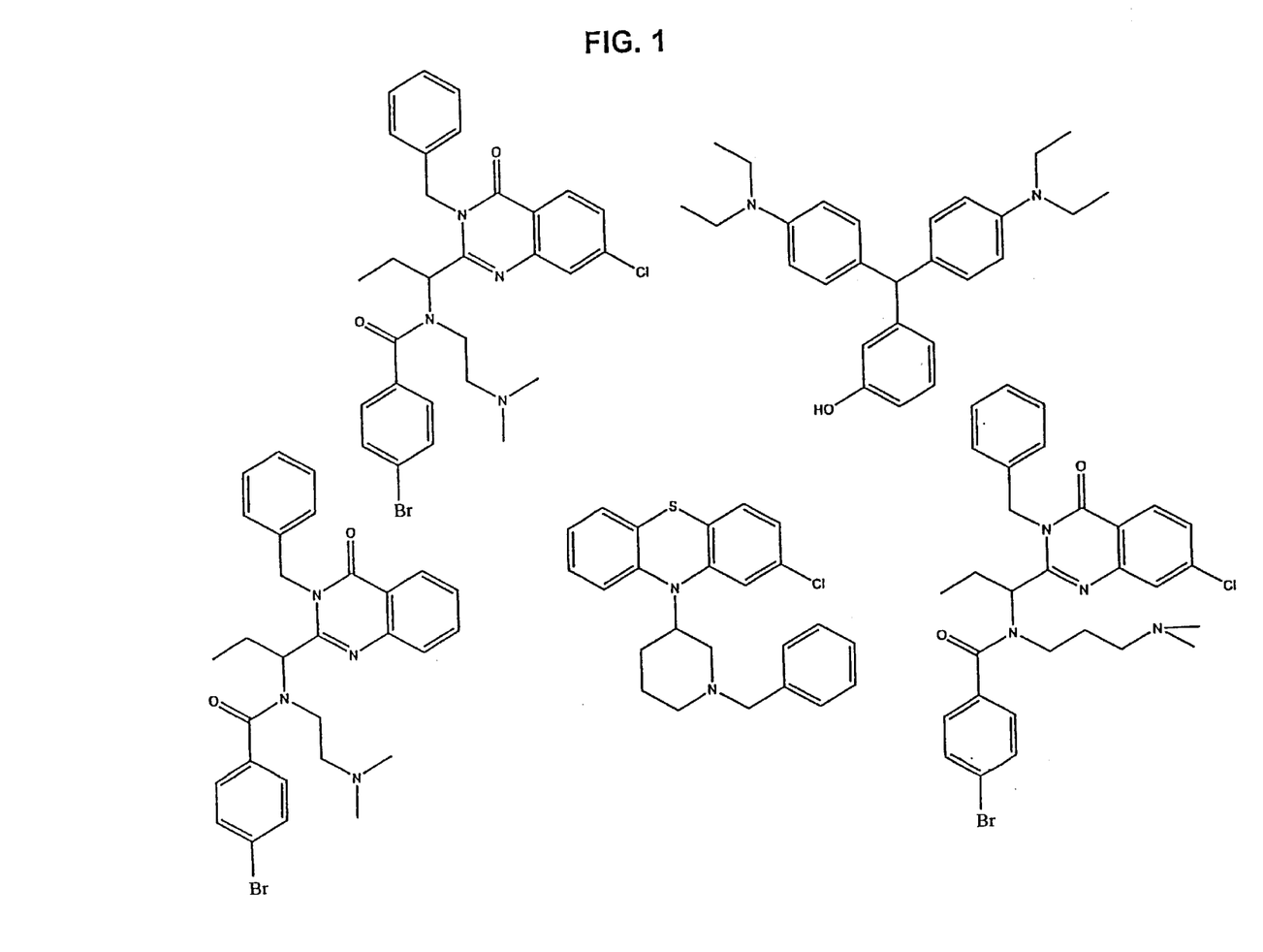
FIG. 1 shows representative KSP inhibitors.

Using the methods as described in Example 1, various KSP inhibitors were identified. Compounds with a detectable effect on the ATPase activity were identified. FIG. 1 shows representative compounds that interact with the Loop 5 region of KSP and thereby modulate the biological activity of KSP.

Example 3

Identification of L5 Loop as the Binding Site of Kinesin Inhibitors

To further confirm that the L5 region of KSP (Gly$^{117}$ to Gly$^{134}$) is the binding site of the KSP inhibitors, KSP L5 was replaced by the L5 loop of KHC (Gly$^{97}$ to Gly$^{106}$). The KSP-KHC hybrid in which L5 of KSP was replaced by a corresponding region (Gly$^{97}$ to Gly$^{106}$) taken from human kinesin heavy chain (KHC) was constructed by conventional methods.

The hybrid KSP protein was found to retain its microtubule stimulated ATPase using assays described in Example 1. The hybrid was also examined for inhibition by the various KSP inhibitors as described in Example 2. The results indicate that except for one inhibitor, which maintained its inhibitory effect on the ATPase activity of the hybrid KSP, the other KSP inhibitors lost their inhibitory effects.

Example 4

Screening of KSP Inhibitors Using L5-Containing Polypeptide

KSP inhibitors are identified by screening test compounds which bind to L5 fragment in a L5-containing polypeptide. In one method, a simplified screening is set up in which only a KSP fragment containing L5 is used. This could be a polypeptide consisting of exclusively KSP sequence or a stretch of KSP sequence embedded into a foreign polypeptide chain. The polypeptide is expressed in a bacteria system, in a phage display system, in a living human or animal cell, or prepared by some combination of such methods. Methods to be used to monitor the binding of test compounds to the L5-containing polypeptide include, but are not limited to, monitored using various methods, e.g., monitoring intrinsic fluorescence of the polypeptide, monitoring fluorescence of the peptide previously modified with a fluorescent marker, monitoring the energetics of the polypeptide unfolding (e.g., by microcalorymetry, circular dichroism, or other methods), identifying molecules binding to the polypeptide attached to the solid support or alternatively detecting the polypeptide binding to the immobilized compound.

Many modifications and variations of this invention can be made without departing from its spirit and scope, as will be apparent to those skilled in the art. The specific embodiments described herein are for illustration only and are not intended to limit the invention in any way.

All publications, figures, patents and patent applications cited herein are hereby expressly incorporated by reference for all purposes to the same extent as if each was so individulily denoted.

What is claimed is:

1. A method for identifying a compound as a kinesin modulator, comprising the steps of:
   (a) contacting said compound with a kinesin or fragment thereof, wherein said kinesin or fragment comprises a L5 loop and wherein said L5 loop includes a tryptophan residue;
   (b) monitoring fluorescence of said tryptophan residue; and (c) correlating said fluorescence to modulation of an activity of said kinesin or fragment thereof, wherein a reduction in fluorescence indicates binding of the compound to said kinesin or fragment thereof.

2. The method of claim 1, wherein the compound is a known inhibitor of the kinesin.

3. The method of claim 1, further comprising contacting the compound with a kinesin molecule or a cell comprising a kinesin molecule, and determining an effect of said compound on a bioactivity of said kinesin.

4. The method of claim 3, wherein said bioactivity is mitosis, ATP hydrolysis, or bipolar spindle formation.

5. The method of claim 4, wherein said compound inhibits the bioactivity of said kinesin.

6. The method of claim 3, wherein said effect is determined by determining an effect on cellular proliferation, cellular viability, motility, or morphology.

7. The method of claim 6, wherein the effect on morphology is the production of a monopolar spindle phenotype.

8. The method of claim 1, further comprising the steps of:

(d) contacting said compound and said kinesin or fragment thereof, with a test compound; and (e) monitoring fluorescence of said tryptophan residue of said kinesin or fragment thereof, wherein a difference between the fluorescence found in step (b) and the fluorescence found in step (e) indicates that the test compound competes with said compound in binding to kinesin or said kinesin fragment.

9. The method of claim 1, wherein said kinesin is KSP.

10. The method of claim 1, wherein said kinesin fragment comprises $Gly^{117}$ to $Gly^{134}$ of the kinesin KSP.

11. The method of claim 1, wherein said kinesin is KHC.

12. The method of claim 1, wherein said kinesin fragment comprises $Glu^{96}$ to $Gly^{106}$ of KHC.

13. The method of claim 1, wherein said kinesin is Kar3.

14. The method of claim 1, wherein said kinesin fragment comprises $Leu^{485}$ to $Gly^{490}$ of Kar3.

15. The method of claim 1, wherein said kinesin is Ncd.

16. The method of claim 1, wherein said kinesin fragment is $Asp^{445}$ to $Gly^{452}$ of Ncd.

* * * * *